(12) United States Patent
Hao et al.

(10) Patent No.: US 11,505,817 B2
(45) Date of Patent: Nov. 22, 2022

(54) METHOD FOR DETECTING AND COUNTING RELATIVE CONTENT OF MICROORGANISM

(71) Applicant: ADVANCED ENERGY & ENVIRONMENTAL TECHNOLOGIES, INC., Beijing (CN)

(72) Inventors: Chun Hao, Beijing (CN); Hai Mei, Beijing (CN)

(73) Assignee: ADVANCED ENERGY & ENVIRONMENTAL TECHNOLOGIES, INC., Beijing (CN)

(*) Notice: Subject to any disclaimer, the term of this patent is extended or adjusted under 35 U.S.C. 154(b) by 655 days.

(21) Appl. No.: 16/483,780

(22) PCT Filed: Mar. 1, 2017

(86) PCT No.: PCT/CN2017/075336
§ 371 (c)(1),
(2) Date: Aug. 6, 2019

(87) PCT Pub. No.: WO2018/145338
PCT Pub. Date: Aug. 16, 2018

(65) Prior Publication Data
US 2021/0062238 A1 Mar. 4, 2021

(30) Foreign Application Priority Data
Feb. 7, 2017 (CN) .................... 201710067710.X (51) Int. Cl.
*C12Q 1/06* (2006.01)
*C12Q 1/64* (2006.01)
*G01N 21/78* (2006.01)

(52) U.S. Cl.
CPC ............ *C12Q 1/06* (2013.01); *C12Q 1/64* (2013.01); *G01N 21/78* (2013.01)

(58) Field of Classification Search
None
See application file for complete search history.

(56) References Cited

U.S. PATENT DOCUMENTS 8,026,093 B2 9/2011 Tung et al.
2014/0162301 A1 6/2014 Marcoux et al.

FOREIGN PATENT DOCUMENTS

CN 101948905 1/2011
CN 102344887 2/2012
(Continued)

OTHER PUBLICATIONS

DiGeronimo et al., Microb. Ecol. 4: 263-266 (1978).*
(Continued)

*Primary Examiner* — Erin M. Bowers
(74) *Attorney, Agent, or Firm* — ParkerHighlander, PLLC (57) ABSTRACT

Provided is a method for detecting and counting the relative content of a microorganism, comprising: adding a redox indicator to a growth medium to produce an indicating growth medium; the range of color variation of the redox indicator comprising three or more colors that can be easily recognized by the naked eye; diluting a sample to be tested, configuring multiple degrees of dilution, configuring multiple parallels for each degree of dilution, and growing the diluted test sample using the indicating growing medium; reading the color or absorbance of the indicating growth medium while growing and/or when growing is completed; and producing the relative content of a microorganism in the test sample on the basis of the level of color variation or the value of absorbance variation of the indicating growth medium.

5 Claims, 4 Drawing Sheets

(56) References Cited

FOREIGN PATENT DOCUMENTS

| CN | 102453746 | 5/2012 |
|---|---|---|
| CN | 102925534 | 2/2013 |
| CN | 103575710 | 2/2014 |
| CN | 103764839 | 4/2014 |

OTHER PUBLICATIONS

Johnsen et al., Appl. Environ. Microbiol. 68(6): 2683-2689 (2002).*
Sigma-Aldrich, "Cell Proliferation Reagent WST-1," https://www.sigmaaldrich.com/deepweb/assets/sigmaaldrich/product/documents/350/519/cellprorobul.pdf, accessed Apr. 5, 2022.*
English translation of Office Action issued in Chinese Patent Application No. 201710067710.X, dated Dec. 3, 2019.
English translation of PCT International Search Report issued in International Application No. PCT/CN2017/075336, dated Oct. 13, 2017.
Mateescu et al., "Comparative analysis of inoculum biomass for biogas potential in the anaerobic digestion," *U.P.B. Scientific Bulletin*, 73(3):99-104, 2011.
Shelef et al., "Rapid optical measurements of microbial contamination in raw ground beef and effects of citrate and lactate," *Journal of Food Protection*, 60(6):673-676, 1997.

\* cited by examiner

METHOD FOR DETECTING AND COUNTING RELATIVE CONTENT OF MICROORGANISM

This application is a US National Phase application based upon PCT Application No. PCT/CN2017/075336, filed Mar. 1, 2017, which claims the priority of Chinese Patent Application No. 201710067710.X, filed with China National Intellectual Property Administration, filed on Feb. 7, 2017, and titled with "METHOD FOR DETECTING AND COUNTING RELATIVE CONTENT OF MICROORGANISM", and the disclosure of which is hereby incorporated by reference.

FIELD

The present invention relates to the field of detection of microorganism, specifically to a method for determining the relative content of a microorganism.

BACKGROUND

The light hydrocarbon gas in the oil and gas reservoir is vertically moved upward along the complex micro-fracture in the form of microbubble floating or continuous gas phase flow driven by reservoir pressure. During the process of light hydrocarbon migration into the surface sediments, a part of it becomes the food (carbon source) of the hydrocarbon-oxidizing bacteria in the soil, which makes the hydrocarbon oxidizing bacteria develop abnormally; the other part is adsorbed by clay minerals or wrapped in secondary carbonate cement. Therefore, microbial anomalies and adsorbed hydrocarbon anomalies that are positively correlated with the abundance and pressure of the underlying oil and gas reservoirs are formed in the surface soil above the oil reservoir. The use of microbiological methods (for example MOST) and geochemical methods (for example SSG) to detect microbial anomalies and adsorbed hydrocarbon anomalies can predict the presence of oil and gas reservoirs in the underlying strata and the nature of the reservoirs. MOST technology is similar to but different from previous oil and gas geochemical exploration. Its main monitoring objective is to explore the abundance of the hydrocarbon-oxidizing bacteria in the soil or sediment above the target area (abbreviated as MV value), and thermogenic hydrocarbon is the sole carbon source of this hydrocarbon-oxidizing bacteria. Therefore, its abundance is closely related to the concentration and pressure of the hydrocarbon hidden in the oil and gas trap below the exploration area, and the index system has the uniqueness of geological interpretation. Most probable number method is a commonly used method to determine abundance of the hydrocarbon-oxidizing bacteria.

Most Probable Number (MPN) method, also known as the dilution culture counting, is one of the commonly used methods in the field of microorganism detection. It is suitable for the determination of a group that does not predominate in a mixed microorganism community but has special physiological functions. It is characterized by using the selectivity of the special physiological functions of the microorganism to be tested to get rid of the interference of other microbial groups, and determining the existence and abundance of the microorganism according to the presenting of the physiological function. The present method is particularly suitable for determining the number of specific physiological groups (such as hydrocarbon oxidation, ammoniation, nitrification, cellulose decomposition, nitrogen fixation, vulcanization and anti-sulfurization bacteria) in soil microorganisms and detecting the number of specific microorganism groups (such as coliform groups) in sewage, milk and other foods.

The MPN method is to dilute the test sample in a series of dilutions, and it is diluted until a small amount (such as 1 ml) of the dilution is inoculated into a fresh medium with little or no growth. According to the lowest dilution without growth and the highest dilution when growth occurs, using the "most probable number" theory, an approximation of the number of bacteria per unit volume of the sample can be calculated. Specifically, after a plurality of 10-fold gradient dilutions of the bacteria solution, the bacteria in a certain amount of the bacteria solution can be very few or none. Then each dilution is taken 3 to 5 replicates and inoculated into a suitable liquid medium. After culture, the number of tubes with microorganism growth from the last three dilutions in which the microorganism grows (i.e. the critical series) is taken as the quantitative index, and the approximate value is found from the most probable number table, and then multiplied by the dilution multiple of the first digit of the quantitative index to obtain the number of bacteria in the original bacteria solution.

The MPN method has certain limitations. For example, the same MPN value may have different meanings, the MPN value is also discontinuous, and the accuracy of the MPN value decreases as the maximum probability (Pmax) decreases. At the time of reading, the standard MPN method only records whether the result of the culture is positive (with bacterial growth) or negative (no bacterial growth), which reduces the accuracy of the MPN method. For example, for a certain replicate samples of a certain dilution in the MPN method, the culture result is positive, but the degree of positivity is different, since the positivity may be caused by a large amount of microorganism growth, or may be caused by a small amount of microorganism growth. For example, two samples, serial dilutions are used, 3 tubes per group, when the numbers of positive tubes are both "3-3-2", the corresponding MPN values are both 1100, but the positive tubes of these two samples may have different degrees of reaction, and the actual microorganism biomass may vary, but the conventional MPN method cannot distinguish such differences.

In addition, at the time of reading, the standard MPN method only takes one reading when culture is performed for a certain period of time, records the number of positive reactions, and looks at the MPN table to obtain the result. A single reading can only record a positive reaction of the medium at a certain incubation time, and its accuracy is not high. For example, two samples with different numbers of microorganisms are cultured in a medium solution. The sample with a large number of microorganisms shows a positive reaction at 6 hours while the sample with a small number of microorganisms shows a positive reaction at 12 hours. If the reading is taken at 12 hours, both samples are recorded as positive, but in fact the numbers of microorganisms in these samples are different.

Therefore, there is a need to provide a method for determining the relative content of a microorganism with more accuracy.

SUMMARY

In view of this, the present disclosure provides a method for determining the relative content of a microorganism. Compared with the conventional MPN method, the method for determining the relative content of microorganism of the present disclosure is more precise and accurate for detecting relative content of microorganism in different samples, and has higher comparability for determining relative content of a microorganism in different samples, and has a wide application.

In order to achieve the above objective, the present disclosure provides the following technical solutions:

The present disclosure provides a method for determining the relative content of a microorganism, comprising the following steps:

Step 1: adding a redox indicator to a medium to obtain an indicator medium; the color change range of the redox indicator includes three or more than three colors that can be easily recognized by a naked eye;

Step 2: diluting a test sample, setting 3 to 15 dilutions, setting 3 to 15 replicates for each dilution, and culturing the diluted test sample using the indicator medium;

Step 3: reading the color or absorbance of the indicator medium during culture and/or after the completion of culture; and Step 4: obtaining the relative content of the microorganism in the test sample according to color change degree or absorbance change value of the indicator medium.

Preferably, the redox indicator is resazurin or methyl blue.

In the embodiments provided by the present disclosure, the redox indicator is resazurin.

In a preferred embodiment provided by the present disclosure, Step 3 is reading the color of the indicator medium after the completion of the culture, and Step 4 is obtaining the relative content of microorganism in the test sample according to the color change degree of the indicator medium as follows:

according to the correlation between the color of the indicator medium and the content of microorganism, reading the color of the indicator medium and giving different color a numerical value, and the numerical value of the reading is positively correlated with the content of microorganism;

using the following formula to obtain the relative content of microorganism in the test sample:

$$Z=(X_{1\text{-}1}+X_{1\text{-}2}+\ldots+X_{1\text{-}n})\times Y_1+(X_{2\text{-}1}+X_{2\text{-}2}+\ldots+X_{2\text{-}n})\times Y_2+\ldots+(X_{m\text{-}1}+X_{m\text{-}2}+\ldots+X_{m\text{-}n})\times Y_m,$$

wherein, Z is the relative content of a microorganism in the test sample; m is the $m^{th}$ dilution, $3 \leq m \leq 15$; n is the $n^{th}$ replicate sample, $3 \leq n \leq 15$; X is the value of a reading, $X \geq 0$; $X_{m\text{-}n}$ represents the value of the reading of the $n^{th}$ replicate sample of the $m^{th}$ dilution; Y represents a dilution coefficient, $Y > 0$; $Y_m$ represents the dilution coefficient of the $m^{th}$ dilution, and $Y_m \geq Y_{m\text{-}1} \geq Y_{m\text{-}2} \geq \ldots Y_2 \geq Y_1$.

In the present disclosure, the numerical value of the reading is positively correlated with the content of microorganism. For example, when no microorganism grows, a relatively small number is used for the color of the indicator itself, and a relatively large number is used when a large number of microorganisms grow and the color of the indicator changes completely. For example, when resazurin indicator is used, according to the content of microorganism, the color change range of the indicator varies from blue to purple to magenta to red and to colorless, and the reading is set as 0, 1, 2, 3, and 4, respectively.

In another preferred embodiment provided by the present disclosure, Step 3 is reading the color of the indicator medium during the culture and after the completion of the culture. The color of the indicator medium is read at least twice during the culture and after the completion of the culture. The color of the indicator medium is read at least once during the culture.

Preferably, the time interval between each reading is evenly or unevenly distributed. For the embodiment in which the time interval between each reading is evenly distributed, the time interval between each reading is the ratio of the total number of culture day to the total number of reading. For the embodiment in which the time interval between each reading is unevenly distributed, the time interval between each reading may be properly adjusted according to the total number of culture day and the total number of reading.

In the preferred embodiment, Step 4, obtaining the relative content of microorganism in the test sample according to the color change degree of the indicator medium, is performed as follows:

according to the correlation between the color of the indicator medium and the content of microorganism, recording the color of the indicator medium as a number, and the number is positively correlated with the content of microorganism;

using the following formula to obtain the final value of one reading:

$$Z_i=(X_{1\text{-}1}+X_{1\text{-}2}+\ldots+X_{1\text{-}n})\times Y_1+(X_{2\text{-}1}+X_{2\text{-}2}+\ldots+X_{2\text{-}n})\times Y_2+\ldots+(X_{m\text{-}1}+X_{m\text{-}2}+\ldots+X_{m\text{-}n})\times Y_m,$$

wherein, $Z_i$ is the final value of one reading; i is the time of color reading of the indicator medium during the culture and after the completion of the culture, $i \geq 2$; m is the $m^{th}$ dilution, $3 \leq m \leq 15$; n is the $n^{th}$ replicate sample, $3 \leq n \leq 15$; X is the value of a reading, $X \geq 0$; $X_{m\text{-}n}$ represents the reading of the $n^{th}$ replicate sample of the $m^{th}$ dilution; Y represents a dilution coefficient, $Y > 0$; $Y_m$ represents the dilution coefficient of the $m^{th}$ dilution, and $Y_m \geq Y_{m\text{-}1} \geq Y_{m\text{-}2} \geq \ldots Y_2 \geq Y_1$;

using the following formula to obtain the relative content of microorganism in the test sample:

$$Z=Z_1+\ldots+Z_i,$$

wherein, Z is the relative content of a microorganism in the test sample; $Z_i$ is the final value of one reading; i is the time of color reading of the indicator medium during the culture and after the completion of the culture, $i \geq 2$.

In another preferred embodiment provided by the present disclosure, Step 3 is reading the absorbance of the indicator medium after the completion of the culture, and Step 4 is obtaining the relative content of microorganism in the test sample according to the absorbance change value of the indicator medium as follows:

using the following formula to obtain the relative content of microorganism in the test sample according to the absorbance change value of the indicator medium:

$$Z=(X_{1\text{-}1}+X_{1\text{-}2}+\ldots+X_{1\text{-}n})\times Y_1+(X_{2\text{-}1}+X_{2\text{-}2}+\ldots+X_{2\text{-}n})\times Y_2+\ldots+(X_{m\text{-}1}+X_{m\text{-}2}+\ldots+X_{m\text{-}n})\times Y_m,$$

wherein, Z is the relative content of a microorganism in the test sample; m is the $m^{th}$ dilution, $3 \leq m \leq 15$; n is the $n^{th}$ replicate sample, $3 \leq n \leq 15$; X is the absorbance change value of the indicator medium; $X_{m\text{-}n}$ represents the absorbance change value of the $n^{th}$ replicate sample of the $m^{th}$ dilution; Y represents a dilution coefficient, $Y > 0$; $Y_m$ represents the dilution coefficient of the $m^{th}$ dilution, and $Y_m \geq Y_{m\text{-}1} \geq Y_{m\text{-}2} \geq \ldots Y_2 \geq Y_1$.

In another preferred embodiment provided by the present disclosure, Step 3 is reading the absorbance of the indicator medium during the culture and after the completion of the culture, and the reading is performed at least twice during the culture and after the completion of the culture. The absorbance of the indicator medium is read at least once during the culture.

In the preferred embodiment, Step 4 is obtaining the relative content of the microorganism in the test sample according to the absorbance change value of the indicator medium as follows:

using the following formula to obtain the final value of one reading of the test sample according to the absorbance change value of the indicator medium:

$$Z_i = (X_{1-1} + X_{1-2} + \ldots + X_{1-N}) \times Y_1 + (X_{2-1} + X_{2-2} + \ldots + X_{2-N}) \times Y_2 + \ldots + (X_{M-1} + X_{M-2} + \ldots + X_{m-n}) \times Y_m,$$

wherein, $Z_i$ is the final value of one reading; i is the time of reading the absorbance change value of the indicator medium during the culture and after the completion of the culture, $i \geq 2$; m is the $m^{th}$ dilution, $3 \leq m \leq 15$; n is the $n^{th}$ replicate sample, $3 \leq n \leq 15$; X is the absorbance change value; $X_{m-n}$ represents the absorbance change value of the $n^{th}$ replicate sample of the $m^{th}$ dilution; Y represents a dilution coefficient, $Y > 0$; $Y_m$ represents the dilution coefficient of the $m^{th}$ dilution, and $Y_m \geq Y_{m-1} \geq Y_{m-2} \geq \ldots Y_2 > Y_1$;

using the following formula to obtain the relative content of microorganism in the test sample:

$$Z = Z_1 + \ldots + Z_i,$$

wherein, Z is the relative content of microorganism in the test sample; $Z_i$ is the final value of one reading; i is the time of reading the absorbance change value of the indicator medium during the culture and after the completion of the culture, $i \geq 2$.

Preferably, the detection wavelength of the absorbance is the maximum absorption wavelength of the redox indicator.

The present disclosure provides a method for determining the relative content of microorganism. The method comprises: adding a redox indicator to a medium to obtain an indicator medium, wherein the color change range of the redox indicator includes three or more than three colors that can be easily recognized by a naked eye; diluting a test sample, setting 3 to 15 dilutions, setting 3 to 15 replicates for each dilution, and culturing the diluted test sample using the indicator medium; reading the color or absorbance of the indicator medium during culture and/or after the completion of culture; and obtaining the relative content of microorganism in the test sample according to color change degree or absorbance change value of the indicator medium. The present disclosure has the following beneficial effects:

1. In the present disclosure, the redox indicator has three or more colors that can be easily recognized by the naked eyes is applied to the MPN method, which can distinguish the degree of positive reaction, and can effectively improve the comparability between the data obtained by the MPN method;

the present disclosure performs multiple readings during the culture, which can further improve the comparability between the data obtained by the MPN method;

it can be seen that compared with the conventional MPN method, the method for determining the relative content of microorganism provided by the present disclosure is more precise and accurate for determining relative content of microorganism in different samples, has higher comparability for detecting relative content of microorganism in different samples, has relatively good data continuity and has a wide application.

2. The present disclosure analyzes the correlation between the method of the present invention, the MPN method and the microscopic counting method, and the results show that the method of the present disclosure is more correlated with the microscopic counting method, and the result is more consistent with the actual situation.

DETAILED DESCRIPTION

The present disclosure discloses a method for determining the relative content of a microorganism. A person having ordinary skill in the art can learn from the content of the present disclosure and appropriately improve the process parameters to achieve it. It is necessary to point out that all similar alternatives and modifications which are obvious to those having ordinary skill in the art are considered to be included in the present invention. The method and the application of the present disclosure have been described with reference to the preferred embodiments and it is obvious that the method and application described herein may be modified or appropriately changed and combined without departing from the content, spirit and scope of the present invention to implement and apply the techniques of the present invention.

The present disclosure provides a method for determining the relative content of a microorganism, comprising the following steps:

1) selecting an indicator having a significant color change range for microorganism growth, and adding the indicator to a medium;

2) following the operation of the conventional MPN method, setting multiple dilutions as needed, setting multiple replicates for each dilution, and culturing;

3) performing reading after culturing for a period of time, recording the change degree of the indicator for microorganism growth when reading;

4) setting multiple reading time points according to the culture time of the microorganism, are performing multiple readings; and 5) calculating the possible content of the microorganism in the sample using the data of the change degree of the indicator obtained in each reading and the result of multiple readings.

Wherein, Step 3) and Step 4) need not to be carried out at the same time, the effect of improving the accuracy of the MPN method can be achieved when Step 3) or Step 4) is carried out alone, but the result is better when they are combined.

Preferably, the microorganism growth indicator having a significant color change range in Step 1) includes resazurin, etc.

Preferably, the change degree of the microorganism growth indicator is read by visual observation or by absorbance measurement using a spectrophotometer.

Preferably, according to the standard that the color difference can be easily recognized by the naked eyes, the color change range of the indicator is divided into three or more colors, the color of the indicator is recorded when reading, and a small to large number is used to represent the indicator color that varies from the color of the indicator itself to the complete color change. When no microorganism grows, a relatively small number is used for the color of the indicator itself, a relatively large number is used when a large number of microorganisms grow and the color of the indicator changes completely.

Preferably, the maximum absorption wavelength of the indicator is used as the light wavelength for the measurement. The absorbance of the culture medium at the beginning of the culture is measured using a spectrophotometer. After culturing for a period of time, the absorbance of the culture medium is measured, and the absorbance change is recorded.

Preferably, the reading time point in Step 4) is 2 or more.

Preferably, the method of calculation in Step 5) is performed by setting coefficient for each dilution, and the coefficient set for the low dilution≤the coefficient set for the high dilution. For the naked eye observation method, the reading of each replicate sample of a certain dilution is multiplied by the coefficient corresponding to the dilution and added together to obtain the result of the dilution. The result of the reading point is obtained by adding the result of each dilution. The final result of the sample is obtained by adding the results of all reading points.

Preferably, the method of calculation in Step 5) is performed by setting coefficient for each dilution, and the coefficient set for the low dilution≤the coefficient set for the high dilution. For the absorbance measurement method, the value of absorbance change obtained by measuring each replicate sample of a certain dilution is multiplied by the coefficient corresponding to the dilution and added together to obtain the result of the dilution. The result of the reading point is obtained by adding the result of each dilution. The final result of the sample is obtained by adding the results of all reading points.

The reagents and instruments used in the method for determining the relative content of microorganism provided by the present disclosure are all commercially available.

The present disclosure is further illustrated below with references to the examples.

Example 1

The samples of this example were collected above an oil and gas trap of a sea area. The marine sediment was collected and the hydrocarbon-oxidizing bacteria in it were detected in order to study the developmental condition of the hydrocarbon-oxidizing bacteria above the oil and gas trap of the sea area.

The specific implementation steps of the method for determining the relative content of microorganism of the present disclosure were as follows:

1. According to the trap structure discovered by geophysical methods, sampling points were arranged in a uniform grid, and 42 samples were collected. The distance between the sample collection sites was 500 m, and the collection depth was 20 cm. The samples were quickly frozen after collection and frozen, and then transported to a testing laboratory where it was stored in a frozen state.

2. 5 g of sample was weighed and put into 20 ml of hydrocarbon-oxidizing bacteria culture medium and mixed to prepare a sample stock solution. The culture medium was referred to the examples in U.S. Pat. No. 5,093,236 (Victoria Gonzales-Prevatt, 1992). The microorganism growth indicator was resazurin.

3. 1 ml of the sample stock solution of Step 2 was pipetted and added to 9 ml of sterilized culture medium, and mixed to prepare a low dilution culture medium. Then, 1 ml of the low dilution culture medium was taken and added to another 9 ml of the sterilized culture medium and mixed to prepare a medium dilution culture medium. Then, 1 ml of the medium dilution culture medium was taken and added to another 9 ml of the sterilized culture medium and mixed to prepare a high dilution culture medium. Three replicate samples were set for each dilution to form a MTN detection system with three dilutions and three replicate samples for each dilution.

4. The MTN detection system was set up as described in steps 2 and 3 for each of the 42 samples. After the completion of the inoculation, the samples were cultured at 24° C. for 15 days.

5. A reading was performed every 3 days. The color of the culture medium was observed when reading. Blue was scored as 0, purple was scored as 1, magenta was scored as 2, red was scored as 3 and colorless was scored as 4.

6. Each reading result was calculated according to the following formula:

$$Z=(X_{1\text{-}1}+X_{1\text{-}2}+\ldots+X_{1\text{-}n})\times Y_1+(X_{2\text{-}1}+X_{2\text{-}2}+\ldots+X_{2\text{-}n})\times Y_2+\ldots+(X_{m\text{-}1}+X_{m\text{-}2}+\ldots+X_{m\text{-}n})\times Y_m,$$

wherein, Z is the final value of the reading; m is the $m^{th}$ dilution; n is the $n^{th}$ replicate sample; $X_{m\text{-}n}$ represents the value of the reading of the $n^{th}$ replicate sample of the $m^{th}$ dilution; Y represents a dilution coefficient; $Y_m$ represents the dilution coefficient of the $m^{th}$ dilution, and $Y_m \geq Y_{m-1} \geq Y_{m-2} \geq \ldots Y_2 \geq Y_1$.

For example, for a certain reading, the reading scores of all replicate samples of the $1^{st}$ dilution (the low dilution) were added together and multiplied by the coefficient 1 of the $1^{st}$ dilution; the reading scores of all replicate samples of the $2^{nd}$ dilution (the medium dilution) were added together and multiplied by the coefficient 2 of the $2^{nd}$ dilution; the reading scores of all replicate samples of the $3^{rd}$ dilution (the high dilution) were added together and multiplied by the coefficient 3 of the $3^{rd}$ dilution. Then the result of the reading was obtained by adding together all the dilution results of multiplying the sum of the replicate samples by the coefficient of each dilution.

The three replicate samples of the $1^{st}$ dilution (the low dilution) were read as 3-3-2, the three replicate samples of the $2^{nd}$ dilution (the medium dilution) were read as 2-2-1, and the three replicate samples of the $3^{rd}$ dilution (the high dilution) were read as 1-1-0. Then the result of the reading was calculated as $(3+3+2)\times1+(2+2+1)\times2+(1+1+0)\times3=24$.

7. The reading was performed every 3 days. Each of a total of five readings was processed according to step 6. Then the results of the five readings were added together to obtain the result of the relative content of microorganism of the sample.

8. Conventional MPN method was used as a control. Only the last reading, i.e. the result of the reading on the $15^{th}$ day, was recorded; and only positive culture medium (purple, magenta, red or colorless) or negative culture medium (blue) was recorded. After recording, the MPN value was obtained by referring to the MPN table.

Figure 1:
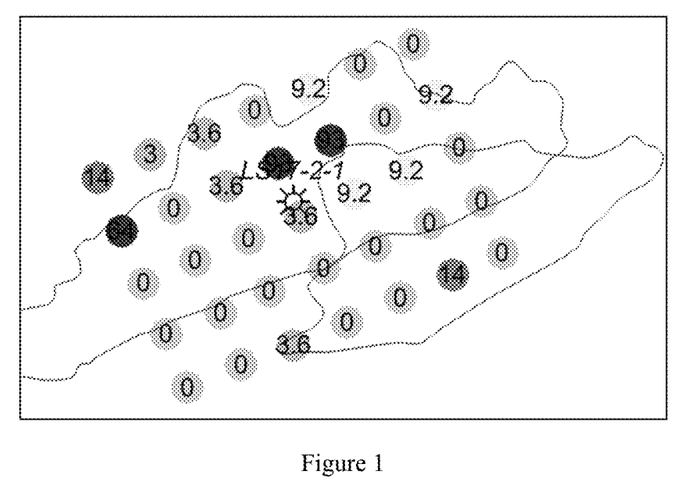
FIG. 1 shows result of determining the relative content of hydrocarbon-oxidizing bacteria in a trap of a sea area using the standard MPN method in Example 1.
Figure 2:
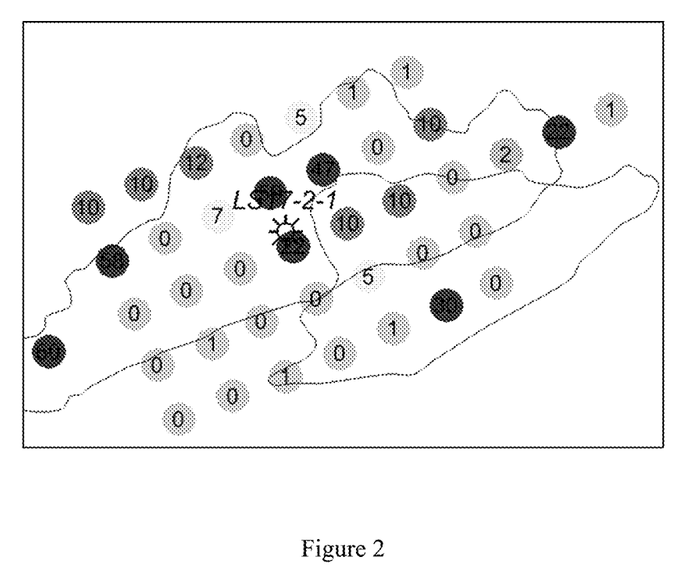
FIG. 2 shows result of determining the relative content of hydrocarbon-oxidizing bacteria in a trap of a sea area using the method provided by the present disclosure in Example 1.

9. The data recorded and processed according to the above-mentioned steps 5 to 7 of the present disclosure were compared with the data recorded and processed according to the above-mentioned step 8. The results are shown in FIGS. 1 and 2. Wherein, FIG. 1 shows the result of determining the hydrocarbon-oxidizing bacteria in a trap of a sea area using the standard MPN method, FIG. 2 shows the result of determining the hydrocarbon-oxidizing bacteria in a trap of a sea area using the method provided by the present disclosure.

It can be seen from FIGS. 1 and 2, the result obtained using the method of the present disclosure has better continuity and accuracy. The four sites with a value of 3.6 by using the standard MPN method were calculated as a result of 12, 7, 22, and 1, respectively, by using the method of the present disclosure, indicating that the result of the present disclosure has better continuity. The result obtained at the drilling site using the present disclosure was a value of 22, which was consistent with the fact that the site was oil and gas well, indicating that the method of the present disclosure has higher accuracy.

Example 2

The samples of this example were collected above an oil and gas reservoir confirmed by drilling of a sea area. The marine sediment was collected and the hydrocarbon-oxidizing bacteria in it were detected in order to study the developmental condition of the hydrocarbon-oxidizing bacteria above the oil and gas trap of the sea area.

The specific implementation steps of the method for determining the relative content of microorganism of the present disclosure were as follows:

1. For an oil and gas reservoir confirmed by drilling of a sea area, sampling points were arranged by survey line, and 23 samples were collected. The distance between the sample collection sites was 500 m, and the collection depth was 20 cm. The samples were quickly frozen after collection and frozen, and then transported to a testing laboratory where it was stored in a frozen state.

2. 5 g of sample was weighed and put into 20 ml of hydrocarbon-oxidizing bacteria culture medium and mixed to prepare a sample stock solution. The culture medium was referred to the examples in U.S. Pat. No. 5,093,236 (Victoria Gonzales-Prevatt, 1992). The microorganism growth indicator was resazurin.

3. 1 ml of the sample stock solution of Step 2 was pipetted and added to 9 ml of sterilized culture medium, and mixed to prepare a low dilution culture medium. Then, 1 ml of the low dilution culture medium was taken and added to another 9 ml of the sterilized culture medium and mixed to prepare a medium dilution culture medium. Then, 1 ml of the medium dilution culture medium was taken and added to another 9 ml of the sterilized culture medium and mixed to prepare a high dilution culture medium. Three replicate samples were set for each dilution to form a MPN detection system with three dilutions and three replicate samples for each dilution.

4. The MPN detection system was set up as described in steps 2 and 3 for each of the 23 samples. After the completion of the inoculation, the samples were cultured at 24° C. for 15 days.

5. A reading was performed after the completion of culture on the $15^{th}$ day. Blue was scored as 0, purple was scored as 1, magenta was scored as 2, red was scored as 3 and colorless was scored as 4.

6. The reading result on the $15^{th}$ day was calculated according to the following formula.

The reading scores of all replicate samples of the low dilution were added together and multiplied by the coefficient 1 of the low dilution; the reading scores of all replicate samples of the medium dilution were added together and multiplied by the coefficient 2 of the medium dilution; the reading scores of all replicate samples of the high dilution were added together and multiplied by the coefficient 3 of the high dilution. Then the result of the reading was obtained by adding together all the dilution results of multiplying the sum of the replicate samples by the coefficient of each dilution, that is, the relative content of microorganism in the sample.

The three replicate samples of the $1^{st}$ dilution (the low dilution) were read as 3-3-2, the three replicate samples of the $2^{nd}$ dilution (the medium dilution) were read as 2-2-1, and the three replicate samples of the $3^{rd}$ dilution (the high dilution) were read as 1-1-0. Then the result of the reading was calculated as $(3+3+2)\times1+(2+2+1)\times2+(1+1+0)\times3=24$.

7. Conventional MPN method was used as a control. Only the last reading, i.e. the result of the reading on the $15^{th}$ day, was recorded; and only positive culture medium (purple, magenta, red or colorless) or negative culture medium (blue) was recorded. After recording, the MPN value was obtained by referring to the MPN table.

Figure 3:
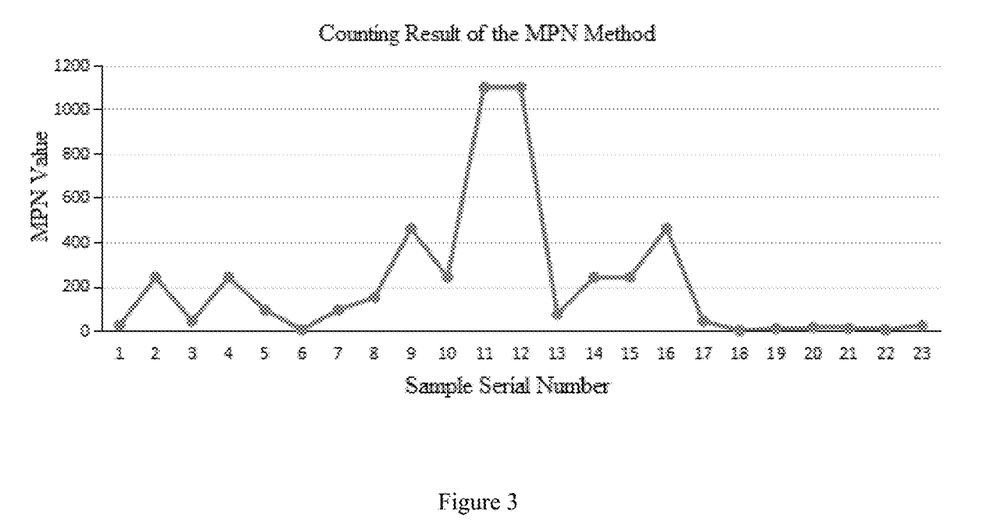
FIG. 3 shows the result of determining the relative content of hydrocarbon-oxidizing bacteria in marine sediment above an oil and gas reservoir of a sea area using the standard MPN method in Example 2.
Figure 4:
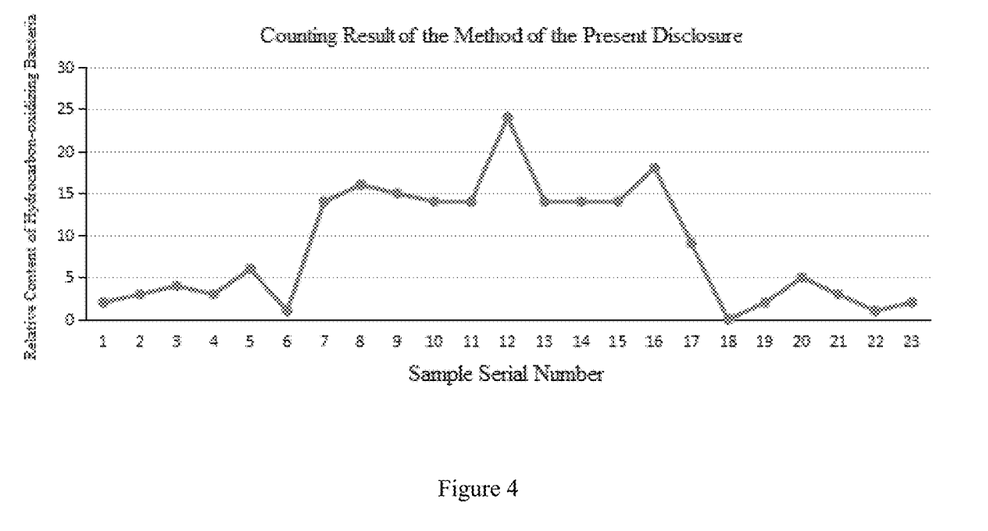
FIG. 4 shows the result of determining the relative content of hydrocarbon-oxidizing bacteria in marine sediments above an oil and gas reservoir of a sea area using the method provided by the present disclosure in Example 2.

8. The data recorded and processed according to the above-mentioned steps 5 to 6 of the present disclosure were compared with the data recorded and processed according to the above-mentioned step 7. The results are shown in FIGS. 3 and 4.

The results show that, confirmed by drilling, the samples numbered 7 to 17 were collected from the oil and gas reservoir area. From the counting result of the method of the present disclosure and the counting result of the MPN method, the counting result of the method of the present disclosure can better reflect the oil and gas reservoir area located between the samples numbered 7 to 17. Samples numbered 7, 8, 10, 13, 14, and 15 gave relatively low values in MPN counting method, while the same samples gave relatively high values in the method of the present disclosure, which was consistent with the actual situation.

Example 3

1. *Acinetobacter* isolated from sea was activated. The activation steps were: the strain was first streaked in a solid culture medium for marine hydrocarbon-oxidizing bacteria, then a single colony was picked and inoculated into the marine hydrocarbon-oxidizing bacteria liquid medium for enrichment culture.

2. The *Acinetobacter* after the enrichment culture was diluted with sterile water to prepare a series of *Acinetobacter* dilutions with 15 different concentrations. The cell numbers in different concentrations were counted by a hemocytometer under a microscope, and the concentrations of *Acinetobacter* in this series of 15 different concentrations were obtained, expressed in unit of cell/ml.

3. 1 ml of the *Acinetobacter* solution of Step 2 was pipetted and added to 9 ml of sterilized culture medium, and mixed to prepare a low dilution culture medium. Then, 1 ml of the low dilution culture medium was taken and added to another 9 ml of the sterilized culture medium and mixed to prepare a medium dilution culture medium. Then, 1 ml of the medium dilution culture medium was taken and added to another 9 ml of the sterilized culture medium and mixed to prepare a high dilution culture medium. Three replicate samples were set for each dilution to form a MPN detection system with three dilutions and three replicate samples for each dilution. The culture medium was referred to the examples in U.S. Pat. No. 5,093,236 (Victoria Gonzales-Prevatt, 1992). The microorganism growth indicator was resazurin.

4. The MPN detection system was set up as described in step 3 for 15 *Acinetobacter* solutions with different concentrations. After the completion of the inoculation, the samples were cultured at 24° C. for 15 days.

5. A reading was performed every 3 days. The color of the culture medium was observed when reading. Blue was scored as 0, purple was scored as 1, magenta was scored as 2, red was scored as 3 and colorless was scored as 4.

6. Each reading result was calculated according to the following formula:

$$Z=(X_{1\text{-}1}+X_{1\text{-}2}+\ldots+X_{1\text{-}n})*Y_1+(X_{2\text{-}1}+X_{2\text{-}2}+\ldots+X_{2\text{-}n})*Y_2+\ldots+(X_{m\text{-}1}+X_{m\text{-}2}+\ldots+X_{m\text{-}n})*Y_m,$$

wherein, Z is the final value of the reading; m is the $m^{th}$ dilution; n is the $n^{th}$ replicate sample; $X_{m\text{-}n}$ represents the value of the reading of the $n^{th}$ replicate sample of the $m^{th}$ dilution; Y represents a dilution coefficient; $Y_m$ represents the dilution coefficient of the $m^{th}$ dilution, and $Y_m \geq Y_{m-1} \geq Y_{m-2} \geq \ldots Y_2 \geq Y_1$.

For example, for a certain reading, the reading scores of all replicate samples of the $1^{st}$ dilution (the low dilution) were added together and multiplied by the coefficient 1 of the $1^{st}$ dilution; the reading scores of all replicate samples of the $2^{nd}$ dilution (the medium dilution) were added together and multiplied by the coefficient 2 of the $2^{nd}$ dilution; the reading scores of all replicate samples of the $3^{rd}$ dilution (the high dilution) were added together and multiplied by the coefficient 3 of the $3^{rd}$ dilution. Then the result of the reading was obtained by adding together all the dilution results of multiplying the sum of the replicate samples by the coefficient of each dilution.

The three replicate samples of the $1^{st}$ dilution (the low dilution) were read as 3-3-2, the three replicate samples of the $2^{nd}$ dilution (the medium dilution) were read as 2-2-1, and the three replicate samples of the $3^{rd}$ dilution (the high dilution) were read as 1-1-0. Then the result of the reading was calculated as $(3+3+2)\times1+(2+2+1)\times2+(1+1+0)\times3=24$.

7. The reading was performed every 3 days. Each of a total of five readings was processed according to step 6. Then the results of the five readings were added together to obtain the result of the relative content of microorganism of the sample.

8. Conventional MPN method was used as a control. Only the last reading, i.e. the result of the reading on the $15^{th}$ day, was recorded; and only positive culture medium (purple, magenta, red or colorless) or negative culture medium (blue) was recorded. After recording, the MPN value was obtained by referring to the MPN table.

At the same time, the numbers of *Acinetobacter* in the above-mentioned samples were counted by microscopic counting.

Figure 5:
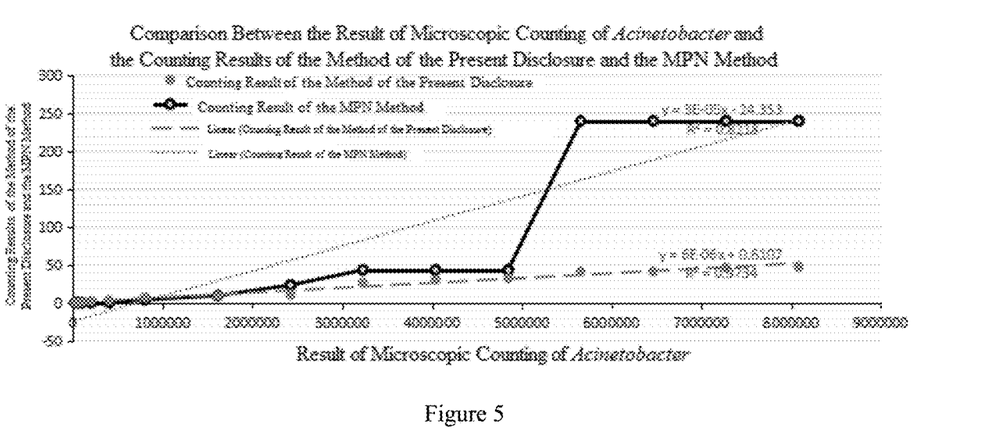
FIG. 5 shows a comparison diagram between the results of microscopic counting and the results of the method of the present disclosure and the MPN method in Example 3 for *Acinetobacter*.

The comparison of the results of microscopic counting, method of the present disclosure and MPN method of the *Acinetobacter* solution with 15 different concentrations are shown in Table 1 and FIG. 5.

TABLE 1

Counting Results of *Acinetobacter* by each method

| No. | Microscopic Counting (cells/ml) | The Present Disclosure | MPN Method (MPN Value/ml) |
|---|---|---|---|
| 1 | 8080000 | 47 | 240 |
| 2 | 7272000 | 46 | 240 |
| 3 | 6464000 | 41 | 240 |
| 4 | 5656000 | 41 | 240 |
| 5 | 4848000 | 32 | 43 |
| 6 | 4040000 | 30 | 43 |
| 7 | 3232000 | 26 | 43 |
| 8 | 2424000 | 10 | 23 |
| 9 | 1616000 | 9 | 9.2 |
| 10 | 808000 | 7 | 3.6 |
| 11 | 404000 | 3 | 0 |
| 12 | 202000 | 2 | 0 |
| 13 | 101000 | 1 | 0 |
| 14 | 50500 | 0 | 0 |
| 15 | 25250 | 0 | 0 |

It can be seen from the above-mentioned figure and table that the results obtained by the method of the present disclosure are significantly better than that of the MPN method, and are more consistent with the results of *Acinetobacter* cell numbers obtained by microscopic counting, the correlation coefficient between the two reached 0.9734, while the correlation coefficient between standard MPN method and microscopic counting was only 0.8218.

Example 4

The samples of this example were collected above an oil and gas reservoir confirmed by drilling of a sea area. The marine sediment was collected and the hydrocarbon-oxidizing bacteria in it were detected in order to study the developmental condition of the hydrocarbon-oxidizing bacteria above the oil and gas trap of the sea area.

The specific implementation steps of the method for determining the relative content of microorganism of the present disclosure were as follows:

1. For an oil and gas reservoir confirmed by drilling of a sea area, sampling points were arranged by survey line, and 23 samples were collected. The distance between the sample collection sites was 500 m, and the collection depth was 20 cm. The samples were quickly frozen after collection and frozen, and then transported to a testing laboratory where it was stored in a frozen state.

2. 5 g of sample was weighed and put into 20 ml of hydrocarbon-oxidizing bacteria culture medium and mixed to prepare a sample stock solution. The culture medium was referred to the examples in U.S. Pat. No. 5,093,236 (Victoria Gonzales-Prevatt, 1992). The microorganism growth indicator was resazurin. The amount of resazurin was adjusted so that the absorbance of the culture medium at 600 nm wavelength was 1.000.

3. 1 ml of the sample stock solution of Step 2 was pipetted and added to 9 ml of sterilized culture medium, and mixed to prepare a low dilution culture medium. Then, 1 ml of the low dilution culture medium was taken and added to another 9 ml of the sterilized culture medium and mixed to prepare a medium dilution culture medium. Then, 1 ml of the medium dilution culture medium was taken and added to another 9 ml of the sterilized culture medium and mixed to prepare a high dilution culture medium. Three replicate samples were set for each dilution to form a MPN detection system with three dilutions and three replicate samples for each dilution.

4. The MPN detection system was set up as described in steps 2 and 3 for each of the 23 samples. After the completion of the inoculation, the samples were cultured at 24° C. for 15 days.

5. A reading was performed after the completion of culture on the 15$^{th}$ day. The absorbance of the culture medium at 600 nm was recorded at the time of reading, and the absorbance value measured after the completion of culture was subtracted from the initial absorbance of 1.000 to obtain an absorbance change value.

6. The reading result on the 15$^{th}$ day was calculated according to the following formula.

The absorbance change values of all replicate samples of the low dilution were added together and multiplied by the coefficient 10 of the low dilution; the absorbance change values of all replicate samples of the medium dilution were added together and multiplied by the coefficient 20 of the medium dilution; the absorbance change values of all replicate samples of the high dilution were added together and multiplied by the coefficient 30 of the high dilution. Then the result of the reading was obtained by adding together all the dilution results of multiplying the sum of the replicate samples by the coefficient of each dilution, that is, the relative content of microorganism in the sample.

The absorbance change values of three replicate samples of the 1$^{st}$ dilution (the low dilution) were 0.752-0.733-0.509; the absorbance change values of three replicate samples of the 2$^{nd}$ dilution (the medium dilution) were 0.560-0.480-0.376; absorbance change values of three replicate samples of the 3$^{rd}$ dilution (the high dilution) were 0.224-0.269-0.109. Then the result of the reading was calculated as (0.752+0.733+0.509)×10+(0.560+0.480+0.376)×20+(0.224+0.269+0.109)×30=66.32.

7. Conventional MPN method was used as a control. Only the last reading, i.e. the result of the reading on the 15$^{th}$ day, was recorded; and only positive culture medium (purple, magenta, red or colorless) or negative culture medium (blue) was recorded. After recording, the MPN value was obtained by referring to the MPN table.

Figure 6:
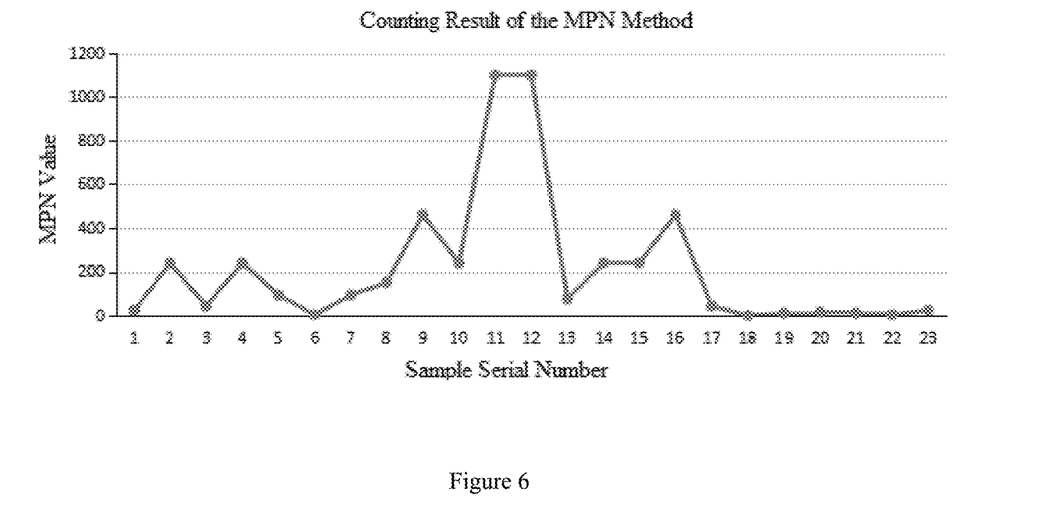
FIG. 6 shows the result of determining the relative content of hydrocarbon-oxidizing bacteria in marine sediment above an oil and gas reservoir of a sea area using the standard MPN method in Example 4.
Figure 7:
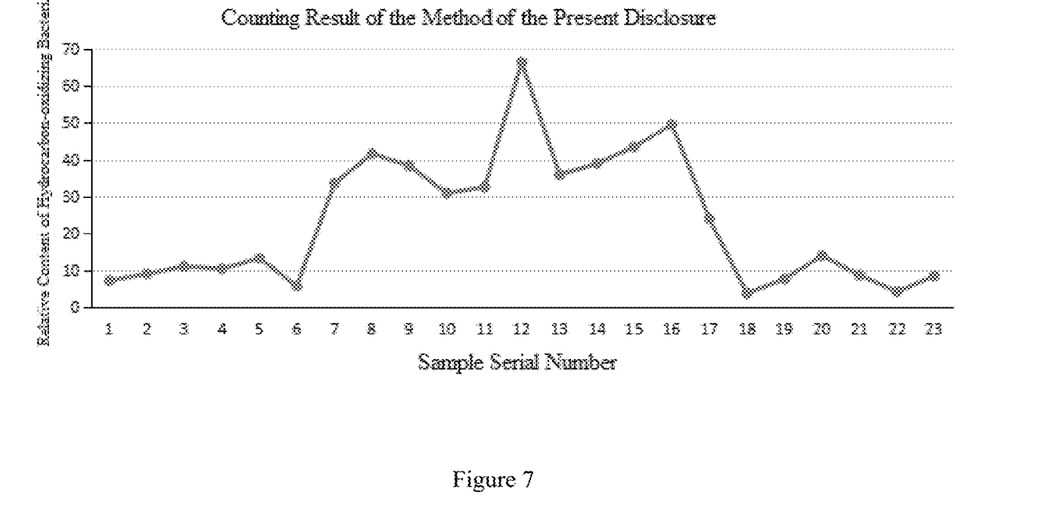
FIG. 7 shows the result of determining the relative content of hydrocarbon-oxidizing bacteria in marine sediment above an oil and gas reservoir of a sea area using the method provided by the present disclosure in Example 4.

8. The data recorded and processed according to the above-mentioned steps 5 to 6 of the present disclosure were compared with the data recorded and processed according to the above-mentioned step 7. The results are shown in FIGS. 6 and 7.

The results show that, confirmed by drilling, the samples numbered 7 to 17 were collected from the oil and gas reservoir area. From the counting result of the method of the present disclosure and the counting result of the MPN method, the counting result of the method of the present disclosure can better reflect the oil and gas reservoir area located between the samples numbered 7 to 17. Samples numbered 7, 8, 10, 13, 14, and 15 gave relatively low values in MPN counting method, while the same samples gave relatively high values in the method of the present disclosure, which was consistent with the actual situation.

The above descriptions are only preferred embodiments of the present disclosure. It should be pointed out that a number of modifications and refinements may be made by those having ordinary skill in the art without departing from the principles of the present invention, and such modifications and refinements are also considered to be within the protection scope of the present invention.

What is claimed is:

1. A method for determining the relative content of a microorganism, comprising the following steps:
   i) adding a redox indicator to a medium to obtain an indicator medium; the color change range of the redox indicator includes three or more colors;
   ii) diluting a test sample 3-15 times with 3-15 replicates of each dilution to produce diluted test samples, and culturing the diluted test samples using the indicator medium;
   iii) reading the color or absorbance of the indicator medium in each diluted test sample during culture and/or after the completion of culture; and
   iv) calculating the relative content of the microorganism in the test sample according to color change or absorbance change value of the indicator medium by:
   according to the correlation between the color of the indicator medium and the content of microorganism, reading the color of the indicator medium in each diluted test sample and giving different color a numerical value, and the numerical value of the reading is positively correlated with the content of microorganism; and
   calculating the relative content of the microorganism in the test sample by a formula of:

$$Z=(X_{1-1}+X_{1-2}+\ldots+X_{1-n})\times Y_1+(X_{2-1}+X_{2-2}+\ldots+X_{2-n})\times Y_2+\ldots+(X_{m-1}+X_{m-2}+\ldots+X_{m-n})\times Y_m,$$

wherein, Z is the relative content of the microorganism in the test sample; m is the m$^{th}$ dilution, 3≤m≤15; n is the n$^{th}$ replicate sample, 3≤n≤15; X is the value of a color reading, X≥0; $X_{m-n}$ represents the value of the reading of the n$^{th}$ replicate sample of the m$^{th}$ dilution; Y represents a dilution coefficient, Y>0; $Y_m$ represents the dilution coefficient of the m$^{th}$ dilution, and $Y_m \geq Y_{m-1} \geq Y_{m-2} \geq Y_2 \geq Y_1$;
   or,
   according to the absorbance change value of the indicator medium, calculating the relative content of the microorganism in the test sample by a formula of:

$$Z=(X_{1-1}+X_{1-2}+\ldots+X_{1-n})\times Y_1+(X_{2-1}+X_{2-2}+\ldots+X_{2-n})\times Y_2+\ldots+(X_{m-1}+X_{m-2}+\ldots+X_{m-n})\times Y_m,$$

wherein, Z is the relative content of the microorganism in the test sample; m is the m$^{th}$ dilution, 3≤m≤15; n is the n$^{th}$ replicate sample, 3≤n≤15; X is the absorbance change value of the indicator medium; $X_{m-n}$ represents the absorbance change value of the n$^{th}$ replicate sample of the m$^{th}$ dilution; Y represents a dilution coefficient, Y>0; $Y_m$ represents the dilution coefficient of the m$^{th}$ dilution, and $Y_m \geq Y_{m-1} \geq Y_{m-2} \geq Y_2 \geq Y_1$.

2. The method for determining the relative content of a microorganism according to claim 1, wherein the redox indicator is resazurin or methyl blue.

3. The method for determining the relative content of a microorganism according to claim 1, wherein reading is reading the color of the indicator medium in each diluted test sample during the culture and after the completion of the culture, and the reading is performed at least twice during the culture and after the completion of the culture; and calculating the relative content of the microorganism in the test sample according to the correlation between the color of the indicator medium and the content of microorganism, recording the color of the indicator medium as a number, and the number is positively correlated with the content of microorganism;

calculating the final value of one reading by a formula of:

$$Z=(X_{1-1}+X_{1-2}+\ldots+X_{1-n})\times Y_1+(X_{2-1}+X_{2-2}+\ldots+X_{2-n})\times Y_2+\ldots+(X_{m-1}+X_{m-2}+\ldots+X_{m-n})\times Y_m,$$

wherein, $Z_i$ is the final value of one reading; i is the times of color reading of the indicator medium during the culture and after the completion of the culture, $i\geq 2$; m is the $m^{th}$ dilution, $3\leq m\leq 15$; n is the $n^{th}$ replicate sample, $3\leq n\leq 15$; X is the value of a color reading, $X\geq 0$; $X_{m-n}$ represents the reading of the $n^{th}$ replicate sample of the $m^{th}$ dilution; Y represents a dilution coefficient, $Y>0$; $Y_m$ represents the dilution coefficient of the $m^{th}$ dilution, and $Y_m\geq Y_{m-1}\geq Y_{m-2}\geq Y_2\geq Y_1$; and calculating the relative content of the microorganism in the test sample by a formula of:

$$Z=Z_1+\ldots+Z_i,$$

wherein, Z is the relative content of the microorganism in the test sample; $Z_i$ is the final value of one reading; i is the times of color reading of the indicator medium during the culture and after the completion of the culture, $i\geq 2$.

4. The method for determining the relative content of a microorganism according to claim 1, wherein reading is reading the absorbance of the indicator medium in each diluted test sample during the culture and after the completion of the culture, and the reading is performed at least twice during the culture and after the completion of the culture; and calculating the relative content of the microorganism in the test sample comprises, according to the absorbance change value of the indicator medium, calculating the final value of one reading of the test sample by a formula of:

$$Z=(X_{1-1}+X_{1-2}+\ldots+X_{1-n})\times Y_1+(X_{2-1}+X_{2-2}+\ldots+X_{2-n})\times Y_2+\ldots+(X_{m-1}+X_{m-2}+\ldots+X_{m-n})\times Y_m,$$

wherein, $Z_i$ is the final value of one reading; i is the times of reading the absorbance change value of the indicator medium during the culture and after the completion of the culture, $i\geq 2$; m is the $m^{th}$ dilution, $3\leq m\leq 15$; n is the $n^{th}$ replicate sample, $3\leq n\leq 15$; X is the absorbance change value; $X_{m-n}$ represents the absorbance change value of the $n^{th}$ replicate sample of the $m^{th}$ dilution, Y represents a dilution coefficient, $Y>0$; $Y_m$ represents the dilution coefficient of the $m^{th}$ dilution, and $Y_m\geq Y_{m-1}\geq Y_{m-2}\geq Y_2\geq Y_1$; and calculating the relative content of the microorganism in the test sample by a formula of:

$$Z=Z_1+\ldots+Z_i,$$

wherein, Z is the relative content of the microorganism in the test sample; $Z_i$ is the final value of one reading; i is the times of reading the absorbance change value of the indicator medium during the culture and after the completion of the culture, $i\geq 2$.

5. The method for determining the relative content of a microorganism according to claim 1, wherein the wavelength for detecting the absorbance is the maximum absorption wavelength of the redox indicator.

* * * * *

UNITED STATES PATENT AND TRADEMARK OFFICE
CERTIFICATE OF CORRECTION

PATENT NO. : 11,505,817 B2  
APPLICATION NO. : 16/483780  
DATED : November 22, 2022  
INVENTOR(S) : Chun Hao and Hai Mei Page 1 of 1

It is certified that error appears in the above-identified patent and that said Letters Patent is hereby corrected as shown below:

In the Claims

In Claim 1, Column 14, Line 37, delete "$Y_m \geq Y_{m-1} \geq Y_{m-2} \geq Y_2 \geq Y_1$" and insert -- $Y_m \geq Y_{m-1} \geq Y_{m-2} \geq \cdots Y_2 \geq Y_1$ -- therefor.

In Claim 1, Column 14, Line 52, delete "$Y_m \geq Y_{m-1} \geq Y_{m-2} \geq Y_2 \geq Y_1$" and insert -- $Y_m \geq Y_{m-1} \geq Y_{m-2} \geq \cdots Y_2 \geq Y_1$ -- therefor.

In Claim 3, Column 15, Line 3, delete "$Z = (X_{1-1} + X_{1-2} + \cdots + X_{1-n}) \times Y_1 + (X_{2-1} + X_{2-2} + \cdots + X_{2-n}) \times Y_2 + \cdots + (X_{m-1} + X_{m-2} + \cdots + X_{m-n}) \times Y_m$" and insert -- $Z_i = (X_{1-1} + X_{1-2} + \cdots + X_{1-n}) \times Y_1 + (X_{2-1} + X_{2-2} + \cdots + X_{2-n}) \times Y_2 + \cdots + (X_{m-1} + X_{m-2} + \cdots + X_{m-n}) \times Y_m$ -- therefor.

In Claim 3, Column 15, Line 12, delete "$Y_m \geq Y_{m-1} \geq Y_{m-2} \geq Y_2 \geq Y_1$" and insert -- $Y_m \geq Y_{m-1} \geq Y_{m-2} \geq \cdots Y_2 \geq Y_1$ -- therefor.

In Claim 4, Column 16, Line 5, delete "$Z = (X_{1-1} + X_{1-2} + \cdots + X_{1-n}) \times Y_1 + (X_{2-1} + X_{2-2} + \cdots + X_{2-n}) \times Y_2 + \cdots + (X_{m-1} + X_{m-2} + \cdots + X_{m-n}) \times Y_m$" and insert -- $Z_i = (X_{1-1} + X_{1-2} + \cdots + X_{1-n}) \times Y_1 + (X_{2-1} + X_{2-2} + \cdots + X_{2-n}) \times Y_2 + \cdots + (X_{m-1} + X_{m-2} + \cdots + X_{m-n}) \times Y_m$ -- therefor.

In Claim 4, Column 16, Line 16, delete "$Y_m \geq Y_{m-1} \geq Y_{m-2} \geq Y_2 \geq Y_1$" and insert -- $Y_m \geq Y_{m-1} \geq Y_{m-2} \geq \cdots Y_2 \geq Y_1$ -- therefor.

Signed and Sealed this  
Fourteenth Day of March, 2023

*Katherine Kelly Vidal*

Katherine Kelly Vidal  
*Director of the United States Patent and Trademark Office*